United States Patent
Burton et al.

[11] Patent Number: 5,141,509
[45] Date of Patent: Aug. 25, 1992

[54] PENILE PROSTHESIS HAVING MEANS FOR PREVENTING SPONTANEOUS INFLATION

[75] Inventors: John H. Burton, Minnetonka; Dezso K. Levius, Bloomington, both of Minn.

[73] Assignee: American Medical Systems, Inc., Minnetonka, Mass.

[21] Appl. No.: 741,004

[22] Filed: Aug. 6, 1991

[51] Int. Cl.⁵ ............................................. A61F 2/02
[52] U.S. Cl. ............................................. 623/11; 600/40
[58] Field of Search ......................... 623/11, 12; 128/79, 128/79 A, 842, 843

[56] References Cited

U.S. PATENT DOCUMENTS

| | | | |
|---|---|---|---|
| 3,683,901 | 8/1972 | Wegener | 128/79 |
| 3,853,122 | 12/1974 | Strauch et al. | 128/79 |
| 3,954,102 | 5/1976 | Buuck | 128/79 |
| 4,342,308 | 8/1982 | Trick | 128/79 |
| 4,353,360 | 10/1982 | Finney et al. | 128/79 |
| 4,399,811 | 8/1983 | Finney et al. | 128/79 |
| 4,407,278 | 10/1983 | Burton et al. | 128/79 |
| 4,412,530 | 11/1983 | Burton | 623/11 |
| 4,550,720 | 11/1985 | Trick | 128/79 A |
| 4,574,792 | 3/1986 | Trick | 128/79 |
| 4,590,927 | 5/1986 | Porter et al. | 128/79 |
| 4,682,583 | 7/1987 | Burton et al. | 128/1 R |
| 4,917,110 | 4/1990 | Trick | 128/79 A |

Primary Examiner—Randy C. Shay
Assistant Examiner—Gina Gualtieri
Attorney, Agent, or Firm—Peter C. Richardson; Lawrence C. Akers; Michael J. Pantuliano

[57] ABSTRACT

An inflatable penile prosthesis having at least one inflatable cylinder or pressurizable chamber, a fluid reservoir, pump means, and valves for permitting the flow of fluid between said reservoir and cylinder or chamber as a consequence of pressure changes, wherein to prevent spontaneous inflation there is provided an additional lock-out valve disposed at a point between the reservoir and chamber, which will be opened only by the application of a suitable pressure or force exerted volitionally from without the prosthesis. In a preferred embodiment the prosthesis is of a non-unitary type in which the pump means is in the scrotum.

9 Claims, 8 Drawing Sheets

PENILE PROSTHESIS HAVING MEANS FOR PREVENTING SPONTANEOUS INFLATION

This invention relates generally to the field of implantable inflatable prosthetic systems for overcoming male erectile impotence, and more specifically to prosthetic penile devices having improved means for preventing spontaneous or involuntary inflation.

A number of devices are available for enabling those with erectile impotence to achieve an erection. These devices are generally implanted within the corpus cavernosum of the penis. Normally two such devices are utilized, one implanted into each corpus cavernosum. Generally speaking, the inflatable penile protheses which are available, or which have been described, include a reservoir, a pump and a pressurized chamber or cylinder. Fluid is pumped from the reservoir to the cylinder or chamber to achieve an erection. Illustrative of the early devices are those disclosed in U.S. Pat. No. 3,853,122 to Strauch, et al., which discloses an external pump and a single tube and valve mechanism, and U.S. Pat. No. 3,954,102 to Buuck, et al., which discloses a device manually operated through the use of bypass valve means.

Unitary penile prostheses which include a pair of concentric chambers, one of which is pressurized, are disclosed in U.S. Pat. Nos. 4,353,360 and 4,399,811. In these patents, the inner of two concentric chambers is pressurized while the outer of the two chambers acts as the fluid reservoir prior to erection. To attain an erection, fluid is pumped from the outer reservoir through a pump to the inner reservoir. Thus, the total volume of the two chambers is always constant.

Further illustrative of the devices available is that disclosed in U.S. Pat. No. 4,590,927 to Porter and Kuyava. This patent relates to a unitary penile prosthesis which comprises a tubular enclosure having a distal portion which includes a pump, a medial portion including a pressurized chamber which contains an internal tubular, substantially non-distensible portion and a concentric tubular sleeve, and a proximal portion defining a fluid reservoir therewithin. The tubular sleeve may elastically bias the non-distensible portion to its flaccid state. A passageway fluidically connects the reservoir and the pump and is in fluid isolation from the pressurizable chamber of the medial portion.

In all of the penile devices available or described the problem of involuntary or spontaneous inflation of the device resulting in an unwanted erection has remained. The problem has been particularly manifested in devices of the non-unitary type, because the latter devices usually have a large reservoir located within the abdomen that is more sensitive to abdominal pressures than are those devices of the unitary type, and accordingly the transfer of fluids to the cylinder implanted in the penis is more affected thereby.

Preferably, the entire act of inflation causing erection should be within the control of the user, but as happens with considerable frequency, a surge of pressure i.e., a pressure "spike," upon the abdomen occasioned by stress, or as a consequence of too-long sitting in one position, or a strenuous exertion, will cause a transient increase in the pressure on the reservoir. This increase of pressure in both unitary or non-unitary devices may very well be above the threshold pressure predetermined to voluntarily initiate inflation, i.e., by the action of the user. When this happens the prosthetic device will often inflate non-voluntarily, causing an unwanted erection with concomitant embarrassment and discomfiture for the user of the device. The need, therefore, exists for a facile, uncomplicated means of preventing such involuntary inflation of the prosthetic device.

U.S. Pat. No. 4,407,278 to Burton et al, discloses a unitary penile prosthesis with improved fluid control. In FIG. 20, 21 and 22, a skirt valve is provided which has the dual functions of permitting the flow of fluid under normal pressurizable conditions, but has an internally disposed membrane which will block, in a non-volitional manner, the flow of liquid which may occur as a consequence of transient or involuntary "spike" pressure changes in the prosthesis, thereby inhibiting spontaneous inflation during the pressure increase. However, it was found that spontaneous inflation would still occur after the transient pressure increase had passed due to fluid that had accumulated in the pump bulb during the increase.

Therefore, none of the prior art devices fully address the desirability for fully volitional means which will afford the user greater control over inflation of the implanted device, and concomitantly, over involuntary or spontaneous inflation of the device. It is thus apparent that a penile prosthetic device which would provide a sure, facile means for preventing or inhibitory involuntary inflation would be very desirable.

SUMMARY OF THE INVENTION

The present invention relates to penile prosthetic devices wherein at least the cylinders or pressurizable chambers thereof are implantable within at least one corpus cavernosum of the penis, each of said devices typically including at least one inflatable cylinder or pressurizable chamber, a fluid reservoir, pumping means, and valves for permitting the flow of liquid between said reservoir and said cylinder or chamber as a consequence of predetermined pressure changes within the prosthesis to effect inflation or deflation of the prosthesis. (It should be noted that within the context of this invention, when the term of art "fluid" is used, this denotes "liquid" only.)

The devices of this invention are preferably characterized by means which are actuated volitionally by the user for preventing or inhibiting spontaneous or involuntary inflation of the devices, said means comprising at least one additional valve disposed at a predetermined designated point along the flow passage between the reservoir and the cylinder or chamber, which valve is designed to remain closed, as desired, until the user applies a predetermined amount of suitable force or pressure from without the prosthesis to open said valve.

In the preferred embodiment, the subject invention comprises a device of a non-unitary type, i.e. with separately disposed inflatable cylinder, fluid reservoir, pump bulb and valves typically of the one-way check type, the latter usually employed to inflate or deflate the prosthesis at the volition of the user in whom the device is implanted. However, in accordance with this invention, there is an additional valve disposed at a predetermined designated point along the flow path between the cylinder and reservoir which valve is of the type which after the cylinder has been deflated after intercourse, is volitionally placed in a closed mode to prevent subsequent involuntary inflation, and thereafter will remain in a closed mode until the user exerts a pressure or force from without the prosthesis sufficient to not only open the valves normally utilized for inflation or deflation but also sufficient to open the additional valve, thereby permitting the transfer of fluid from the reservoir to the cylinder. This added safety or "lock-out" valve will normally not open under the stimulus of a brief or transient pressure "spike" but will only do so when the user volitionally commands it to do so by the aforesaid predetermined sustained application of suitable pressure or force. In practice, the one-way check valves will continue to open or close as in the prior art devices during pumping, but their opening under a transient pressure spike will not normally allow for spontaneous or involuntary inflation because the additional safety or lock-out valve will remain, as stated, closed until "commanded" to open by the completely volitional action of the user, i.e., by the actuation of a suitable predetermined force or pressure which will be exerted to a degree and/or for a time period usually beyond that of the essentially transient pressure "spikes." Only then will the device be inflated.

In a specific embodiment of this invention, the additional valve is preferably of a bi-stable type. The latter can be defined as a valve which will remain in any one of two positions unless directed to one or the other position by a volitional action. Such a valve is manually placed in an inoperative closed position to prevent flow of liquid from the reservoir into the cylinder or pressurizable chamber. It is only opened by the application of a further predetermined pressure generated by volitionally squeezing the pump bulb. It should be noted that the aforesaid valve, e.g. of a bi-stable type, is not a substitution for the one-way check valves which function to allow fluid to be pumped from the fluid reservoir to the cylinder or pressurizable chamber, but is, as stated, an additional valve which will remain closed, preventing or inhibiting the flow of fluid from the reservoir to the cylinder, until the user applies sufficient added pressure to not only open the valve normally functioning to permit flow of fluid from the reservoir to the cylinder but also to open this additional, e.g. bi-stable, valve. The combination of degree or extent of pressure, plus time, is needed to accomplish this. The involuntary pressure surges which may function to open the first check valve will not ordinarily be sufficient in degree of pressure and/or extent of time to open the additional valve.

In another embodiment, the additional lock-out valve may be of the type which is automatically opened by manually squeezing the pump. In this embodiment, a mechanical element capable of being deformed when the bulb is squeezed, is typically disposed within the pump bulb, or less preferably, is disposed in close proximity but in integral association with the pump bulb. When the pump bulb is thereupon squeezed, the aforesaid element is deformed in a manner effective to act upon, and to open, the additional valve according to this invention, i.e. one other than the one-way valves usually employed. As a consequence the same "lock-out" feature previously indicated is accomplished, i.e. spontaneous inflation will similarly be prevented or substantially inhibited, since the additional valve will still usually open to permit flow of liquid from the reservoir to the cylinder only when sufficient volitional force is exerted on the pump bulb by the user of the prosthesis, or his surrogate.

Other embodiments will become evident from the drawings and the description thereof which follow:

DETAILED DESCRIPTION OF THE DRAWINGS

Figure 1:
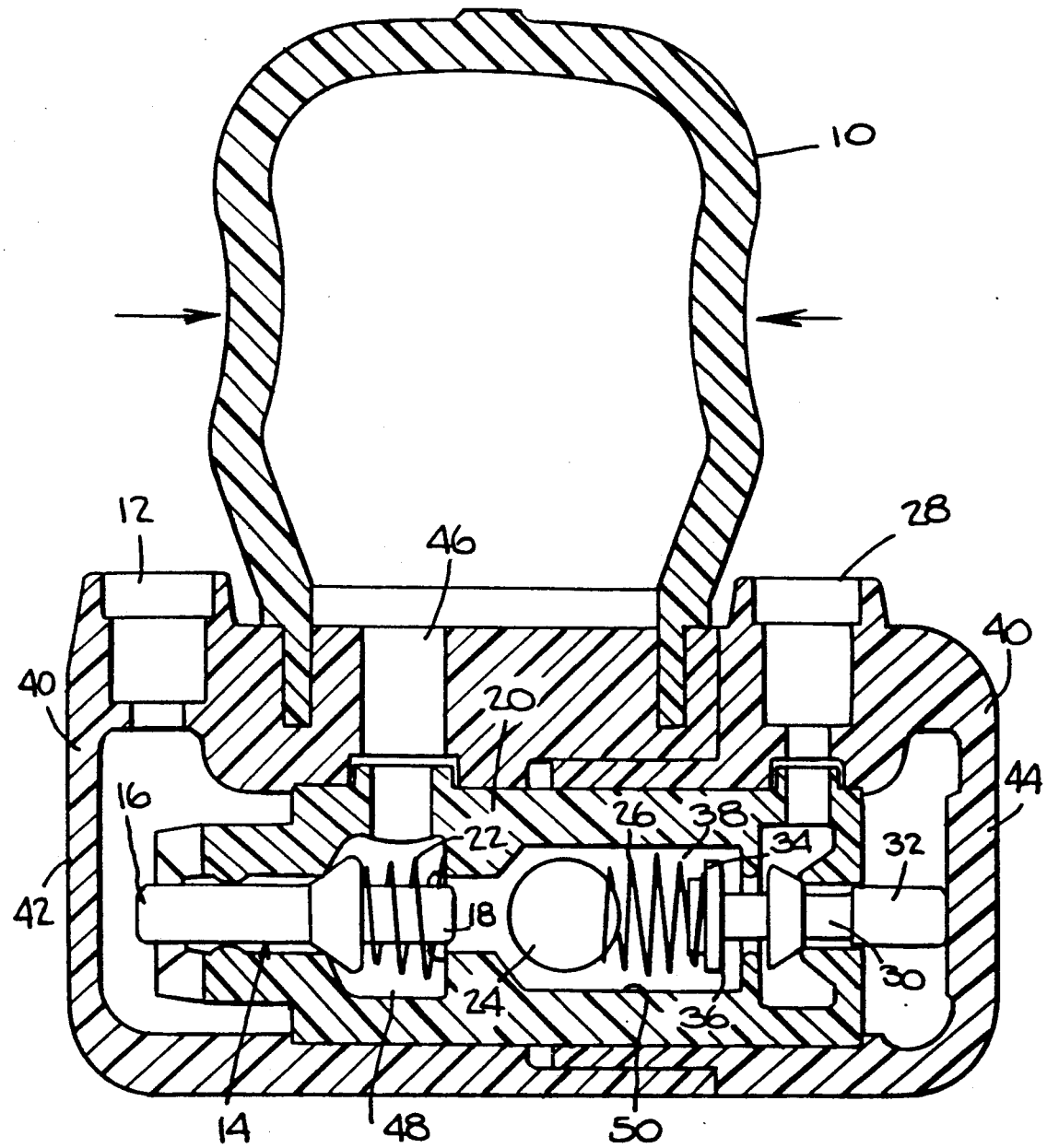
FIG. 1 is a cross-sectional view of a pump bulb and associated valves including one-way check and ball valves and an additional lock-out bi-stable valve of this invention, said pump bulb and valves being shown in the initial pumping phase.

Referring to the drawings wherein like reference characters are utilized for like parts throughout the several views, a portion of a penile prosthesis of the non-unitary type is shown in FIG. 1 in the state which would follow the implantation of the prosthesis (which can be done by any of the methods known in that art).

In FIG. 1 a pump bulb 10, typically of the manually compressible type, is in fluid communication with a fluid reservoir (not shown) inserted in the abdomen or in a corpus cavernosum of the penis (also not shown) through a passageway 12 through check valve 14. The latter, as shown, comprises a stem 16, and a poppet 18. The valve 14 is normally held in sealing contact with valve housing 20 by precalibrated spring 22. In proximity to check valve 14 is ball valve 24 which in the embodiment shown is held in normally closed mode by means of precalibrated spring 26.

Pump bulb 10 is also in fluid communication with a pressurizable chamber or cylinder (not shown) through passageway 28. A lock-out bi-stable valve 30 is disposed in proximity to ball valve 24 in fluid communication with passageway 28. Lock-out valve 30 is formed of a poppet 32 having (illustratively) two heads 34 and 36, which are integral with spring 38.

At each end of the valve outer housing 40 containing the aforesaid valves and passageways, are two deformable surfaces 42 and 44. These surfaces, if desired, can also contain outwardly extending buttons (not shown) which can be used to assist in the deformation of surfaces 42 and 44. Depending downstream from the pump bulb 10 is passageway 46 which enables fluid from the pump bulb to flow into the valves contained in the housing 40.

As stated above, in FIG. 1 the pump bulb is depicted in its initial pumping phase; the initial squeezing of the pump has placed the check valve 14 in a closed mode, abutting as shown with the (interior) valve housing 20. The closing of this valve is due to the pressure exerted in the chamber 48 which extends about the valve 14 which pressure results from the depending flow of liquid down-stream from the pump bulb when the latter is initially squeezed. In this state, ball valve 24 is in the open mode as is bi-stable valve 30.

Figure 2:
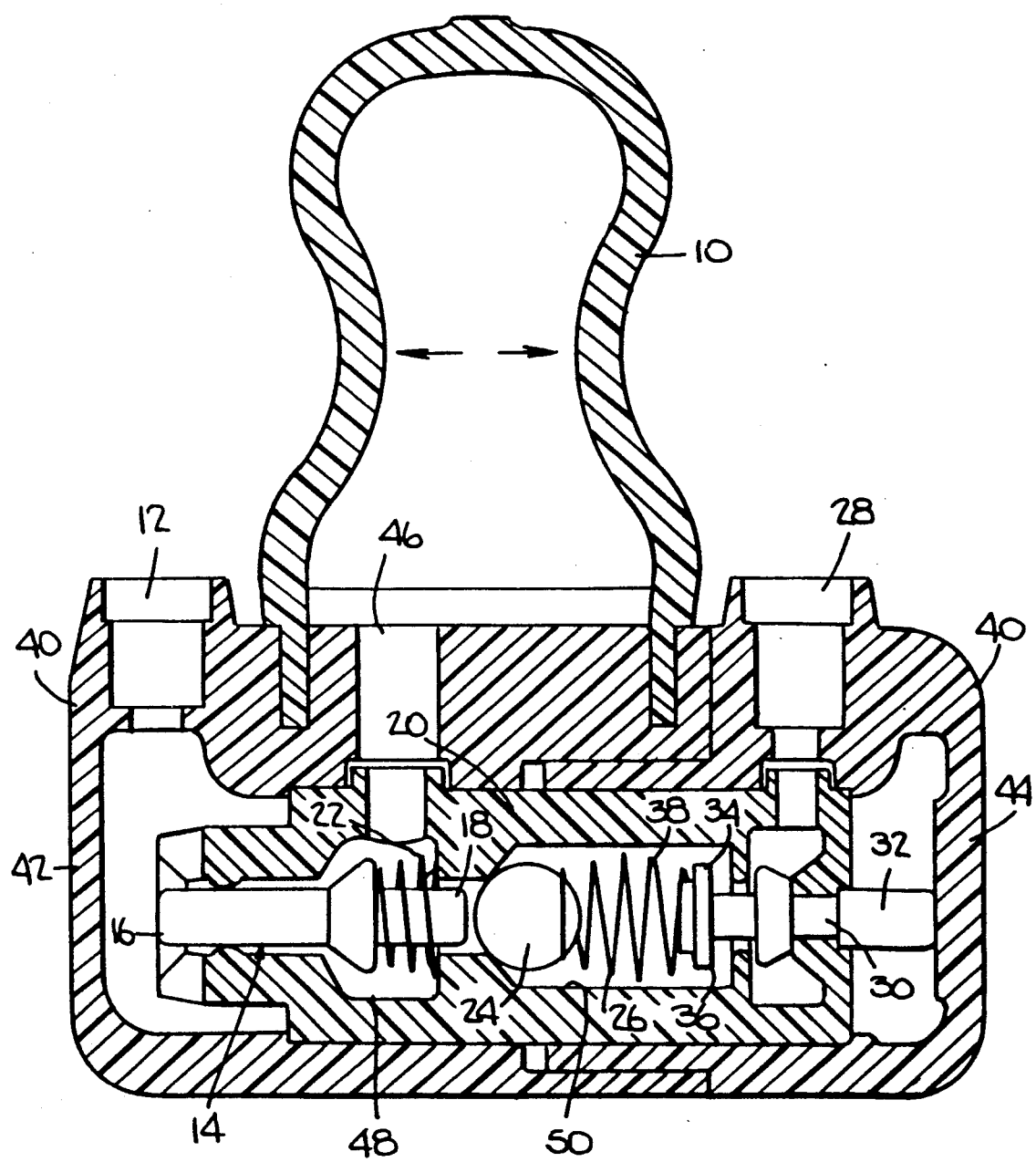
FIG. 2 is a cross-sectional view of the pump bulb and valves of FIG. 1 during the suction phase.

FIG. 2 depicts the attitudes of the valves during the suction phase, when after repeated squeezings the one-way check valve 14 is now open, but the ball valve 24 is now closed as a consequence of the fluid pressure now exerted in chamber 50 which causes the ball valve 24 to abut as shown with another end of interior housing 20. Bi-stable valve 30 is still in an open mode.

Figure 3:
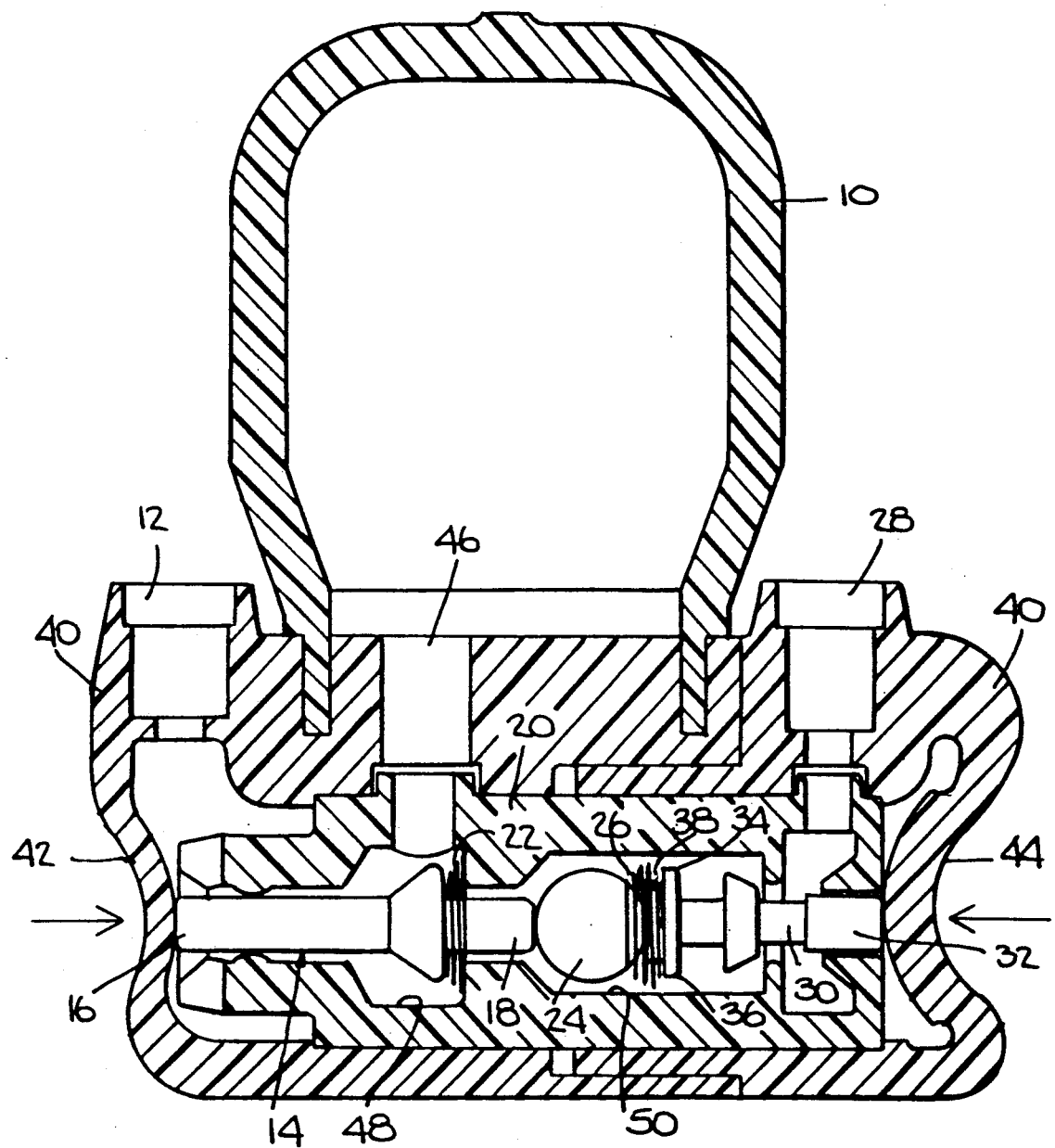
FIG. 3 is a cross-sectional view of the pump bulb and valves of FIG. 1 during the deflation phase.

FIG. 3 depicts the deflation phase which occurs when deformable surfaces 42 and 44 (which are normally composed of silicone rubber or other biologically acceptable elastomer) are squeezed manually by the user. The axially applied force on surface 42 deforms this surface and moves the poppet 18 of valve 14 to its open position as a consequence of the internal pressure produced thereby; the poppet also unseats the ball valve 24 thus opening the passage through channel 28. The equally applied force also deforms the outer surface 44 forcing poppet 32 away from this abutting relationship thus permitting the flow of fluid from the cylinder back to the reservoir, thus effecting deflation. All valves are thus held open by this manual force until suitable flaccidity is accomplished.

Figure 4:
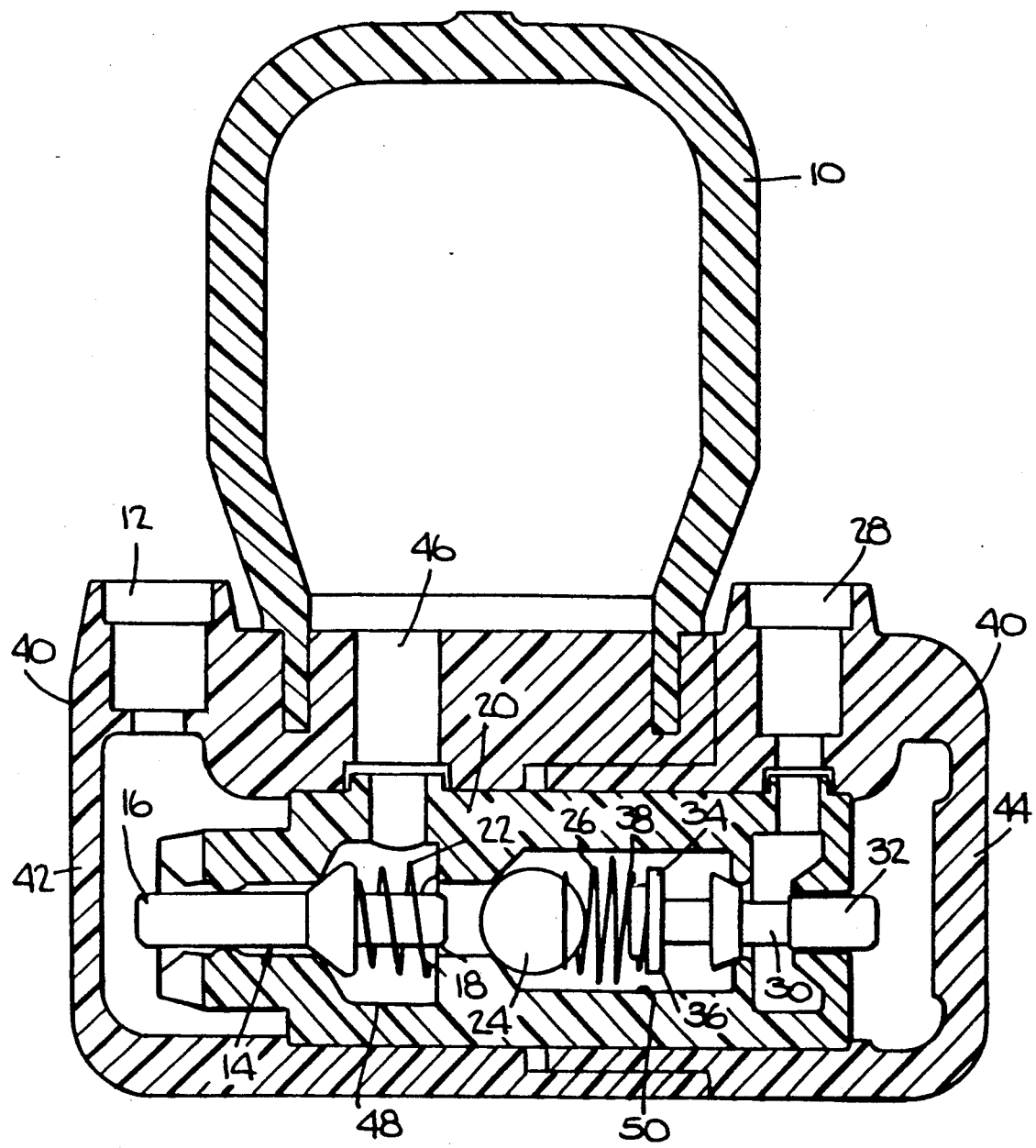
FIG. 4 is a cross-sectional view of the pump bulb and valves of FIG. 1 in which the lock-out mode of the invention is depicted.

FIG. 4 depicts the final stage of the cycle wherein when the force is removed from the valve block or assembly the valves 14 and 24 are closed by the removal of force, thus closing the passageway from the reservoir. In like manner, the bi-stable lock-out valve 30 is also closed due to action of the force of spring 38 thus preventing fluid from passing to the cylinder.

Accordingly, to cause involuntary inflation a transient or pressure spike acting on the reservoir or pump bulb will have to open all three valves of the embodiment shown. The seal between the poppet 32 is typically such that hydraulic pressures of up to 7.0 psi will not open this lock-out valve, such pressures usually being above that of a transient or "spike" type. A pressure exerted by the user of between about 9.0 psi and about 15.0 psi is required to open the valve 30, i.e. thus eliminating the seal of the poppet 32. Only in this manner is the valve deactivated, i.e. its bi-stable mode will then be open, thus permitting a new inflation and erection.

Figure 5:
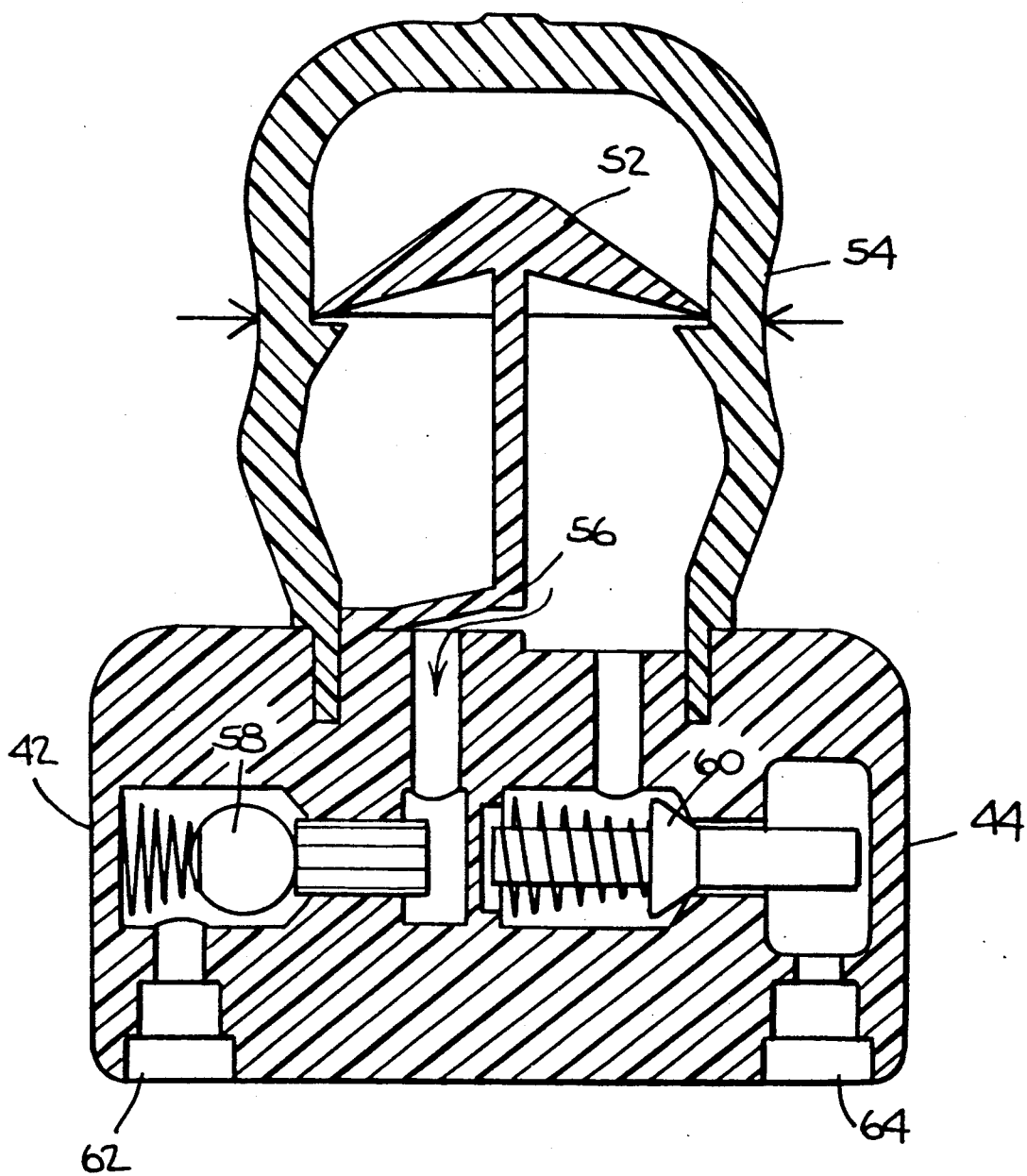
FIG. 5 is a cross-sectional view of another embodiment of this invention in which a deformable mechanical element is shown within a pump bulb wherein the lock-out valve is in an open mode.
Figure 6:
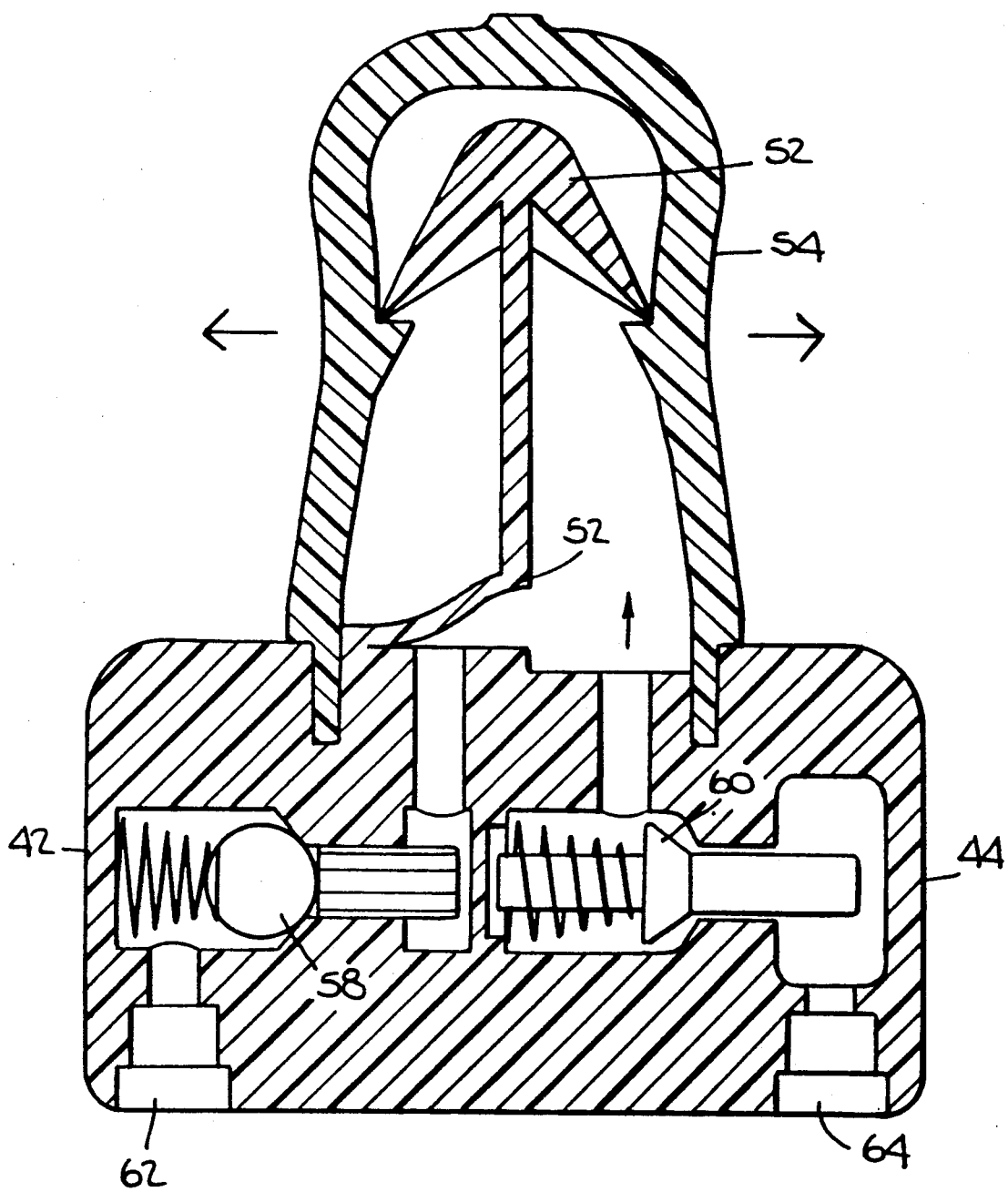
FIG. 6 is a cross-sectional view of the embodiment of FIG. 5 during the suction phase.

In FIG. 5 there is depicted a further embodiment of this invention in which a deformable mechanical device 52 is disposed within a pump bulb 54. The structure of the device 52 is not narrowly critical but should be of the type which upon the squeezing of the pump bulb with sufficient force will act to open a valve 56, the latter typically, in this embodiment, being of a flap type. Again, the shape of the valve 56 is not narrowly critical. As shown in FIG. 5, a mushroom-shaped mechanical device 52 is employed which is in hinged relationship with the valve 56. One-way ball 58 and check valve 60 which function in the manner indicated in FIGS. 1-4, are also disposed in coacting relationship with the valve 56. These are in turn in flow relationship with a cylinder (not shown) through passageway 62 and a reservoir (not shown) through passageway 64. The force to be exerted on the pump bulb by the user must be of a pre-calibrated magnitude, in order to deform the mushroom-shaped mechanical device 52, and thus act to open the flap-type valve 56 and check valve 60. FIG. 6 depicts the mushroomed-shaped device 52 in a deformed position with valves 56 and 60 in open mode. As a consequence, fluid will flow from the reservoir to the pump bulb.

Figure 7:
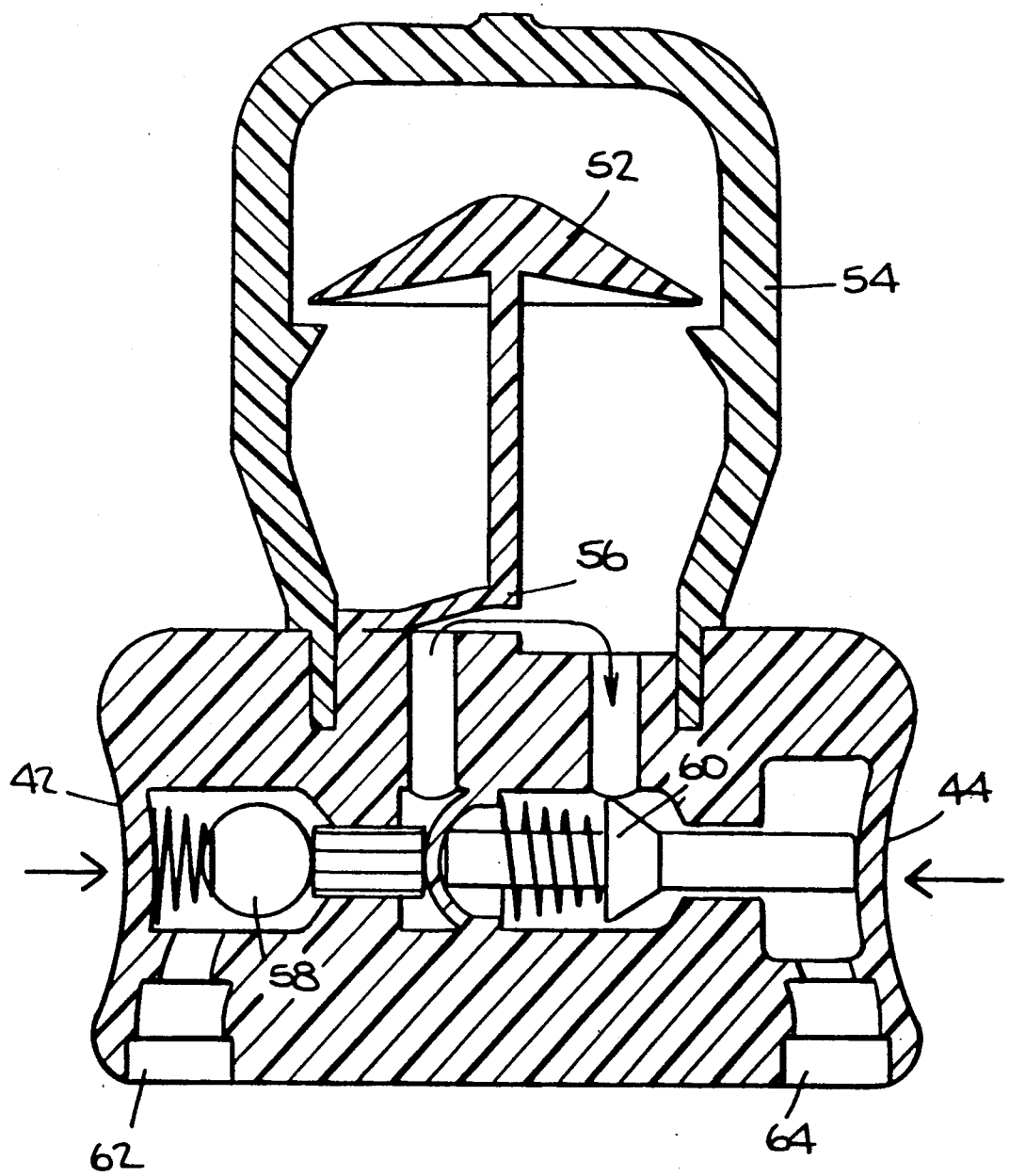
FIG. 7 is a cross-sectional view of the embodiment of FIG. 5 during the deflation phase.
Figure 8:
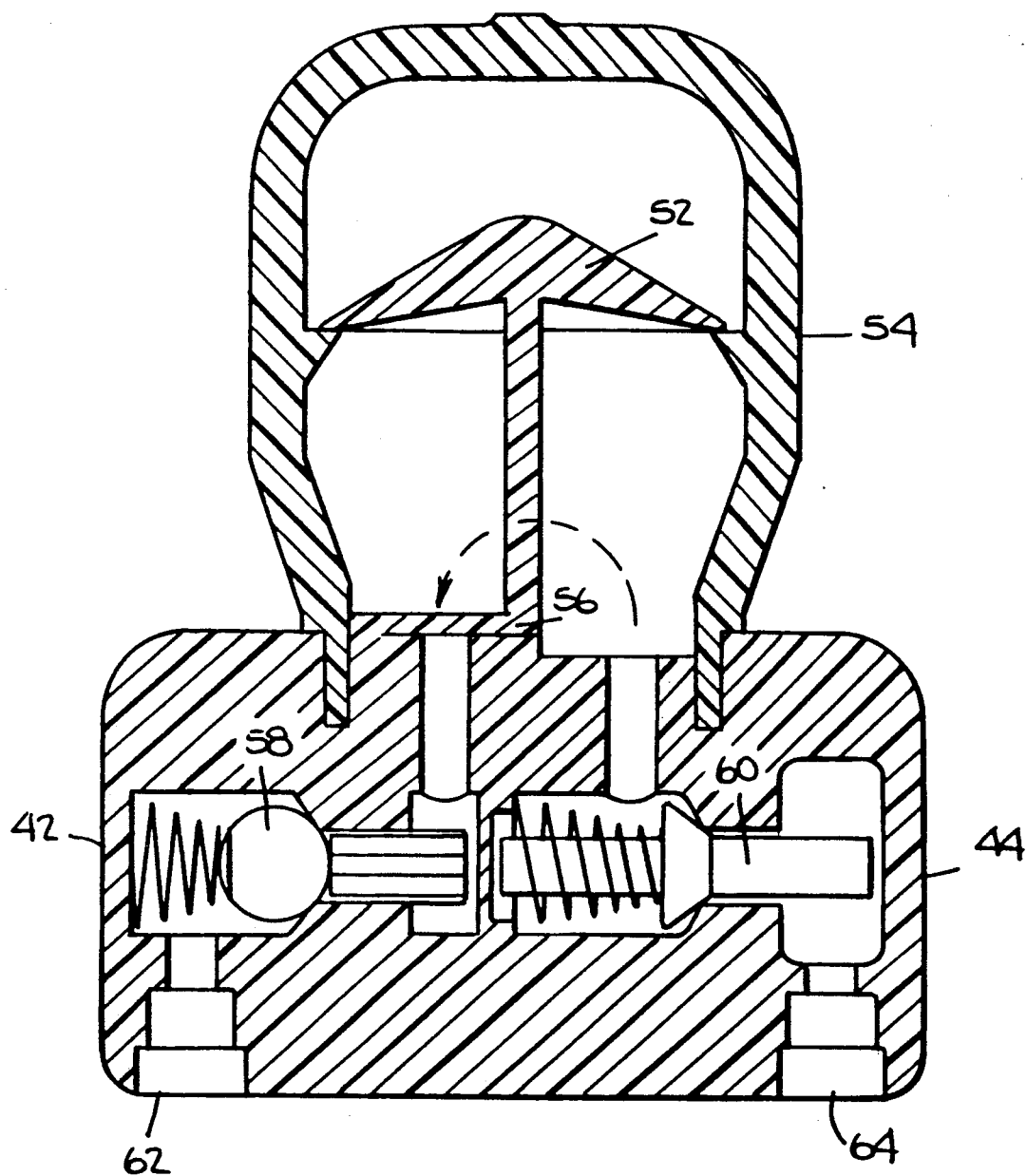
FIG. 8 is a cross-sectional view of the embodiment of FIG. 5 in which the lock-out mode of the invention is depicted.

In a manner similar to FIG. 3, FIG. 7 depicts the deflation phase of the mechanical embodiment represented by device 52. Deflation occurs when deformable surfaces 42 and 44 are squeezed manually by the user. The axially applied forces on surfaces 42 and 44 result in their deformation which, as shown in FIG. 7, results in all the valves assuming the open mode whereby fluid flows back from the cylinder through the pump bulb 54 (through flap valve 56 which remains open) and then back to the reservoir, thus affecting deflation and suitable flaccidity. FIG. 8 depicts the final stage of this embodiment wherein, when the force is removed from the surfaces 42 and 44, valves 52 and 60 return to a closed mode. As a consequence, passageway 64 is also closed thus preventing flow of fluid from the reservoir. "Lock-out" flap valve 56 also returns to its closed mode because the force of internal pressure keeping it open has been removed.

As with the embodiment represented by FIGS. 1-4, a transient or pressure "spike" would have to open all three valves of the embodiment represented by FIG. 5-8 in order for involuntary inflation to occur. In this mechanical embodiment, this would be virtually impossible, i.e., only pressure exerted manually from without the mushroom device 52 would be able to deform the device; without such deformation, flap valve 56 could not (in all likelihood) be opened.

However, it should be noted that from the aspect of practicality in manufacturing, the embodiment of FIGS. 1-4 is preferable to the embodiment represented by FIGS. 5-8.

It should also be again understood that while the present invention is preferably directed to use in non-unitary penile prosthesis, with virtually no modifications in structure and disposition the subject invention can also suitably be used in unitary devices as well.

It is also apparent that modifications and variations beside those specifically mentioned herein may be made in the structures and techniques described herein and depicted in the accompanying drawings without departing from the overall concept of the subject invention.

We claim:

1. An inflatable penile prosthesis comprising means for causing or maintaining erection of a penis, said means having at least one inflatable cylinder or pressurizable for insertion into the penis, a fluid reservoir, pump means, and valves for permitting the flow of fluid between said reservoir and said cylinder or chamber as a consequence of predetermined pressure changes within the prosthesis, and an additional valve disposed at a predetermined designated point along the flow passage between the reservoir and the cylinder or chamber, said additional valve acting to prevent the spontaneous inflation of the prosthesis occasioned by the unwanted transfer of fluid from the reservoir to the cylinder or chamber by remaining closed, as desired, until opened by the application of suitable predetermined pressure or force exerted volitionally from without the prosthesis.

2. An inflatable penile prosthesis comprising means for causing or maintaining erection of a penis, said means having at least one inflatable cylinder or pressurizable chamber for insertion into the penis, a fluid reservoir, pump means, and valves for permitting the flow of fluid between said reservoir and said cylinder or chamber as a consequence of predetermined pressure changes within the prosthesis, and an additional valve disposed at a predetermined designated point along the flow passage between the reservoir and the cylinder or chamber, said additional valve being initially disposed in a closed mode, said additional valve being capable of remaining in said closed mode to prevent or substantially inhibit the inadvertent or involuntary flow of fluid from said reservoir to said cylinder or chamber, until a predetermined pressure or force is exerted upon said valve volitionally by the user from outside the prosthesis sufficient to place said valve in an open mode, thereby again permitting the flow of fluid from the reservoir to the cylinder or chamber to effect inflation of the prosthesis.

3. An inflatable penile prosthesis comprising means for causing or maintaining erection of a penis, said means having at least one inflatable cylinder or pressurizable chamber for insertion into the penis, a fluid reservoir, pump means, and valves for permitting the flow of fluid between said reservoir and said cylinder or chamber as a conquence of predetermined pressure changes within the prosthesis, and an additional valve disposed at a predetermined designated point along the flow passage between the reservoir and the cylinder or chamber, said additional valve being initially disposed in a closed mode and in coacting relationship with mechanical means disposed within the pump means which acts to open or close said additional valve, said additional valve being capable of remaining in said closed mode to prevent or substantially inhibit the inadvertent or involuntary flow of fluid from said reservoir to said cylinder or chamber, until a predetermined force is exerted upon the mechanical means by a user of the prosthesis volitionally squeezing the pump means from outside the prosthesis to the extent sufficient to place said additional valve in an open mode, thereby permitting the flow of fluid from the reservoir to the cylinder or chamber to effect inflation of the prosthesis.

4. An inflatable penile prosthesis according to claims 2 or 3, wherein the inflatable penile prosthesis is nonunitary having a separately disposed fluid reservoir and separately disposed pump means.

5. An inflatable penile prosthesis according to claim 2 wherein the additional valve is disposed at a point between the pump means and the cylinder or chamber.

6. An inflatable penile prosthesis according to claim 2, wherein the additional valve is a bi-stable valve.

7. An inflatable prosthesis according to claim 2 in which the pump means is a pump bulb.

8. An inflatable prosthesis according to claim 3, in which the pump means is a pump bulb.

9. An inflatable penile prosthesis according to claim 8, wherein the mechanical means is an umbrella shaped device having at least two arms which will depend downward upon squeezing said pump bulb to open said additional valve, and which will return to original position when the pump bulb is released to return said additional valve to the closed mode.

* * * * *

REEXAMINATION CERTIFICATE (2783th)

United States Patent [19]
Burton et al.

[11] B1 5,141,509
[45] Certificate Issued  Jan. 23, 1996

[54] PENILE PROSTHESIS HAVING MEANS FOR PREVENTING SPONTANEOUS INFLATION

[75] Inventors: John H. Burton, Minnetonka; Dezso K. Levius, Bloomington, both of Minn.

[73] Assignee: American Medical Systems, Inc., Minnetonka, Minn.

Reexamination Request:
No. 90/003,438, May 17, 1994

Reexamination Certificate for:
Patent No.: 5,141,509
Issued: Aug. 25, 1992
Appl. No.: 741,004
Filed: Aug. 6, 1991

[51] Int. Cl.⁶ ............................................. A61F 2/02
[52] U.S. Cl. .................................... 623/11; 600/40
[58] Field of Search ................ 623/11, 12; 606/191, 606/196; 600/38, 39, 40, 29, 30

[56] References Cited

U.S. PATENT DOCUMENTS

| | | | |
|---|---|---|---|
| 4,404,968 | 9/1983 | Evans | 128/79 |
| 4,407,278 | 10/1983 | Burton | 128/79 |
| 4,550,720 | 11/1985 | Trick | 128/79 |

*Primary Examiner*—David J. Isabella

[57] ABSTRACT

An inflatable penile prosthesis having at least one inflatable cylinder or pressurizable chamber, a fluid reservoir, pump means, and valves for permitting the flow of fluid between said reservoir and cylinder or chamber as a consequence of pressure changes, wherein to prevent spontaneous inflation there is provided an additional lock-out valve disposed at a point between the reservoir and chamber, which will be opened only by the application of a suitable pressure or force exerted volitionally from without the prosthesis. In a preferred embodiment the prosthesis is of a non-unitary type in which the pump means is in the scrotum.

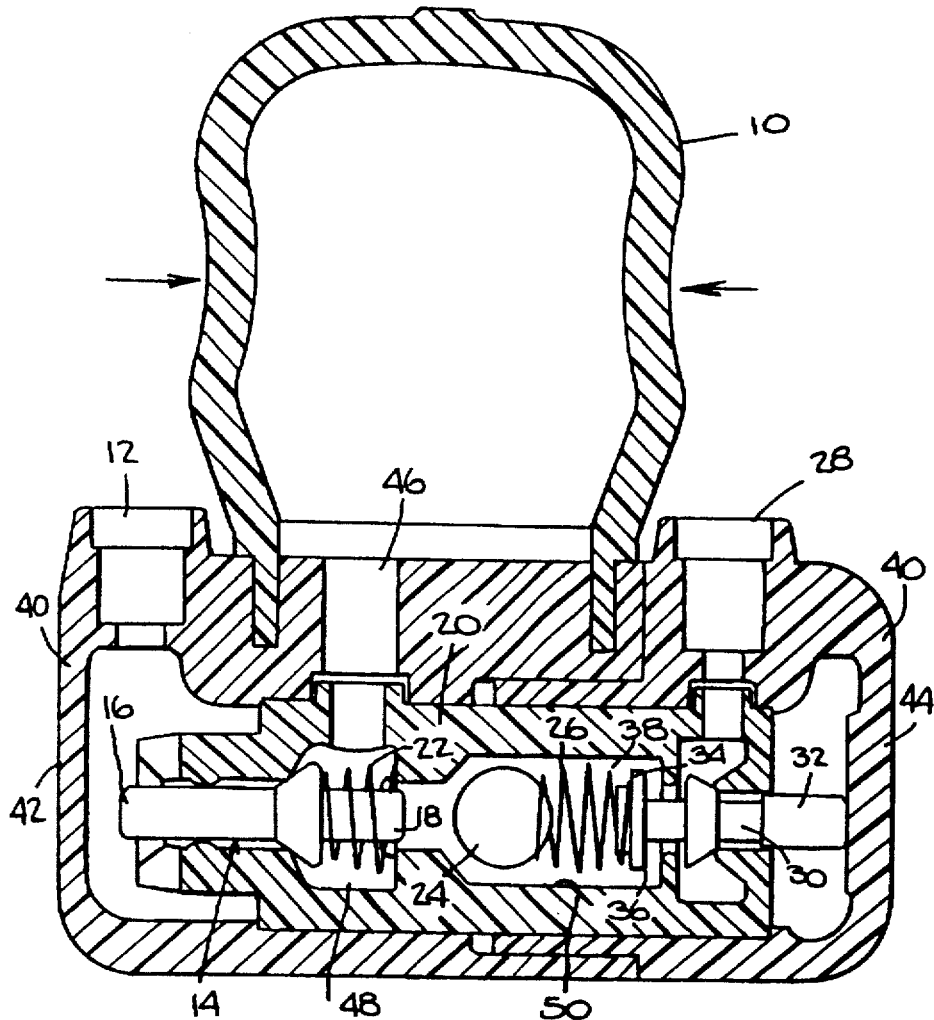

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 3, 8 & 9 is confirmed.

Claim 6 is cancelled.

Claims 1 & 2 are determined to be patentable as amended.

Claims 4, 5 & 7, dependent on an amended claim, are determined to be patentable.

1. An inflatable penile prosthesis comprising means for causing or maintaining erection of a penis, said means having at least one inflatable cylinder or pressurizable *chamber* for insertion into the penis, a fluid reservoir, pump means, and valves for permitting the flow of fluid between said reservoir and said cylinder or chamber as a consequence of predetermined pressure changes within the prosthesis, and an additional valve disposed at a predetermined designated point along the flow passage between the reservoir and the cylinder or chamber, *said additional valve being a bi-stable valve having an open mode in which fluid is permitted to flow through said additional valve and a closed mode in which fluid is unable to flow through said additional valve, said additional valve being designed to remain in the open mode or the closed mode unless directed to the other mode by a volitional force,* said additional valve acting to prevent the spontaneous inflation of the prosthesis occasioned by the unwanted transfer of fluid from the reservoir to the cylinder of chamber by remaining closed, as desired, until opened by the application of suitable predetermined pressure or force exerted volitionally from without the prosthesis.

2. An inflatable penile prosthesis comprising means for causing or maintaining erection of a penis, said means having at least one inflatable cylinder or pressurizable chamber for insertion into the penis, a fluid reservoir, pump means, and valves for permitting the flow of fluid between said reservoir and said cylinder or chamber as a consequence of predetermined pressure changes within the prosthesis, and an additional valve disposed at a predetermined designated point along the flow passage between the reservoir and the cylinder or chamber, *said additional valve being a bi-stable valve having an open mode in which fluid is permitted to flow through said additional valve and a closed mode in which fluid is unable to flow through said additional valve, said additional valve being designed to remain in the open mode or the closed mode unless directed to the other mode by a volitional force,* said additional valve being initially disposed in [a] *the* closed mode, said additional valve being capable of remaining in said closed mode to prevent or substantially inhibit the inadvertent or involuntary flow of fluid from said reservoir to said cylinder or chamber, until a predetermined pressure or force is exerted upon said valve volitionally by the user from outside the prosthesis sufficient to place said valve in [an] *the* open mode, thereby again permitting the flow of fluid from the reservoir to the cylinder or chamber to effect inflation of the prosthesis.

* * * * *